(12) United States Patent
Coffer

(10) Patent No.: US 6,569,292 B2
(45) Date of Patent: May 27, 2003

(54) METHOD AND DEVICE FOR FORMING A CALCIUM PHOSPHATE FILM ON A SUBSTRATE

(75) Inventor: Jeffery L. Coffer, Fort Worth, TX (US)

(73) Assignee: Texas Christian University, Ft. Worth, TX (US)

( * ) Notice: Subject to any disclaimer, the term of this patent is extended or adjusted under 35 U.S.C. 154(b) by 167 days.

(21) Appl. No.: 09/825,728

(22) Filed: Apr. 4, 2001

(65) Prior Publication Data
US 2002/0144888 A1 Oct. 10, 2002

(51) Int. Cl.⁷ ................................................ B01J 19/08
(52) U.S. Cl. ....................... 204/164; 427/540; 427/2.27; 427/419.2
(58) Field of Search ........................... 204/164; 427/540, 427/2.27, 419.2

(56) References Cited

U.S. PATENT DOCUMENTS

| 5,614,220 A | 3/1997 | Hirakawa et al. | ............ 424/480 |
|---|---|---|---|
| 5,676,997 A | * 10/1997 | Okuyama et al. | ........... 427/2.26 |
| 5,814,550 A | 9/1998 | Wolcott | ........................ 435/402 |
| 6,033,582 A | 3/2000 | Lee et al. | ......................... 216/37 |
| 6,153,266 A | * 11/2000 | Yokogawa et al. | ......... 427/2.27 |

* cited by examiner

Primary Examiner—Kishor Mayekar
(74) Attorney, Agent, or Firm—Charles D. Gunter, Jr.

(57) ABSTRACT

A method of forming thin porous layers of calcium phosphate upon a silicon wafer surface using a high voltage spark. The outer layer of calcium phosphate is the inorganic component of bone and is anchored to the underlying substrate of silicon. The silicon is compatible with existing integrated circuit processing methods. The morphology and thickness of the calcium phosphate film can be controlled by the duration of the spark and the distance between the affected surface and the counterelectrode utilized. The resultant porous layer can be impregnated with medicinally useful substances which then can be subsequently released to the surroundings through an electrical actuator.

18 Claims, 4 Drawing Sheets

METHOD AND DEVICE FOR FORMING A CALCIUM PHOSPHATE FILM ON A SUBSTRATE

BACKGROUND OF THE INVENTION

1. Field of the Invention

The present invention relates generally to devices and methods for forming fixed calcium phosphate films on isolating substrates, more specifically, upon semiconducting substrates. In a preferred application, the calcium phosphate film thus formed is used as a drug delivery system which effects the controlled release of a medicinally active ingredient to a targeted site over a predetermined time interval.

2. Description of the Prior Art

Techniques are known in the prior art for applying inorganic films to isolating substrates, such as silicon substrates. The previous methods have generally either involved high energy plasma deposition techniques which were complicated and expensive to implement or involved wet chemical etch type techniques. The wet chemical etch techniques in some cases resulted in contaminating the substrates to be coated, thereby impairing the function of the components to be manufactured from the substrate. See, for example, "Bioreactive Silicon Structure Fabrication Through Nano-etching Techniques", Advanced Materials, 1995,7, No. 12. Dry coating methods are also known in various arts, including cathode sputtering and vapor deposition. These techniques are primarily used to deposit metal layers over the entire surface of a target substrate, sometimes with the aid of a mask whose openings correspond to the pattern to be deposited. These masks are relatively complicated to manufacture and their alignment relative to the substrate must be extremely accurate.

A need exists for a simple technique for permanently or semi-permanently afixing an inorganic film, such as a calcium phosphate film, to an isolating substrate. As will be explained, such films are biocomapatible and can be used to dispense medicinally active agents.

The controlled release of a medicinally active ingredient at a specific location or in reaction to a specific environmental condition has long been desired in the medical community. One promising method is to modify a silicon wafer base to carry or store medicine. Previous techniques for modifying the silicon wafer base to carry or store medicine have generally involved an etching process to create pores in the surface.

U.S. Pat. No. 6,033,582, issued Mar. 7, 2000, to Lee et al., shows one method for modifying a wafer base in which non-uniform relief patterns are created on the silicon by exposing the surface to a reactive plasma. The reactive plasma produces a reaction product to etch the surface of the silicon thus creating reservoirs to store the material. However, it is expensive and difficult to generate the plasma. The nature of this process may handicap the commercial viability of the technique. Another known method used generally for applying films to silicon substrates involves the two step wet chemical etch discussed above to form a film on the silicon surface. Again, this method is expensive as well as time consuming.

What is needed is a method for fabricating a thin porous layer on a silicon substrate and a method and apparatus for the timed or environmentally conditioned release of an active agent from the porous layer.

SUMMARY OF THE INVENTION

One object of the present invention is to provide a simple method and apparatus for applying an inorganic film to an isolating substrate.

Another object of the present invention is to provide a method for fabricating a thin porous film on a silicon substrate. In the preferred embodiment of the invention, a calcium phosphate film is fixed in permanent or semi-permanent fashion to a substrate.

It is another object of the present invention to provide a method and apparatus for the timed or environmentally conditioned release of an active agent from a calcium phosphate film which has been afixed upon a silicon substrate.

Another object of the invention is to provide such a method which can be implemented as a dry method, if desired. The dry method does not contaminate the substrate to be coated with wet chemicals and since no baths are utilized, there are no adverse environmental disposal problems created.

The foregoing objects are achieved by the device and method of the invention. The method of the invention provides for the selective, self-aligned deposition of a calcium phosphate film to a selected region of an isolating substrate. The isolating substrate is first exposed with calcium phosphate to form a coating upon the selected region. The coated region of the substrate is then subjected to a high voltage spark, whereby a fixed calcium phosphate film having a desired morphology and thickness is formed within the selected region of the substrate.

The outer layer of calcium phosphate is the inorganic component of bone and is anchored to the underlying substrate of silicon which is compatible with existing integrated circuit processing methods. The morphology and thickness of the calcium phosphate film can be controlled by such factors as the duration of the spark and the distance between the coated silicon substrate and an electrode or counter-electrode. The resultant layer of calcium phosphate is porous in nature and can be impregnated with medicinally useful substances which then can be subsequently released to the surroundings through electrical actuating means. The electrical actuating means can be formed integrally with the substrate by known integrated circuit manufacturing techniques.

In a preferred method of the invention, there is provided a method for the selective, self-aligned deposition of a calcium phosphate film to a selected region of a silicon substrate. The silicon substrate is first exposed with calcium phosphate to form a coating. An electrode is then positioned a predetermined distance from the coating on the substrate. A current is then generated between the electrode and the substrate by capacitively coupling an RF power source to a selected one of the electrode and coated substrate, the resulting current creating a spark which forms a fixed calcium phosphate film having a desired morphology and thickness within the selected region of the substrate.

If desired, the porous calcium phosphate film which is formed can then be impregnated with an active agent to be released over a predetermined time interval. In order to accomplish the timed release of the active agent, an electrical actuating means is provided, including as preferred components thereof a power supply, a CPU and electrical connection to the calcium phosphate film all of which components are mounted or formed upon the semiconducting substrate using known integrated circuit manufacturing techniques. The preferred electrical actuating means further includes a sensor for detecting selected environmental conditions, the sensor being electrically connected to the CPU, whereby the sensor causes the CPU to trigger a release of the active agent upon detection of a preselected environmental condition. In the preferred embodiment of the invention, the active agent is a medicament with the device containing the medicament being implanted or otherwise introduced within the body of a human being or other living creature. The electrical actuating means can be signaled to release the medicament over a predetermined time interval.

The above as well as additional objectives, features, and advantages of the present invention will become apparent in the following detailed written description.

DETAILED DESCRIPTION OF THE PREFERRED EMBODIMENT

The method of the invention provides a technique for the selective, self-aligned deposition of a calcium phosphate film to a selected region of an isolating substrate. Calcium phosphate is the inorganic component of human bone and, as such, is bicompatible. Calcium phosphate exists in various phases of compounds including: (1) amorphous calcium phosphates; (2) brushite or dicalcium phosphate dihydrate, $CaHPO_4$ $2H_2O$; (3) monetite or dicalcium phosphate anhydrous, $CaHPO_4$; (4) octacalcium phosphate, $Ca_8H_2(PO_4)_6$ $5H_2O$; (5) whitlockite or tricalcium phosphate, $Ca_3(PO_4)_2$; and apatite, calcium-OH-apatite, idealized as $Ca_{10}(PO_4)_6(OH)_2$. The preferred formulation of the calcium phosphate phase used in the experiments which follow was hydroxyapatite, $Ca_{10}(PO_4)_6(OH)_2$ although the other forms of calcium phosphate or even amorphous calcium phosphate could be utilized as well. The calcium phosphate film of the invention is used to coat an isolating substrate to form a porous medium which can be used to dispense active agents, including medicinally active agents.

By "isolating substrate" is meant that the substrate can be made of an isolating material, such as a plastic or ceramic material, or of a semiconductive material, such as silicon. The preferred isolating material is a silicon wafer of the type commercially available for semiconductor device manufacture.

Figure 1:
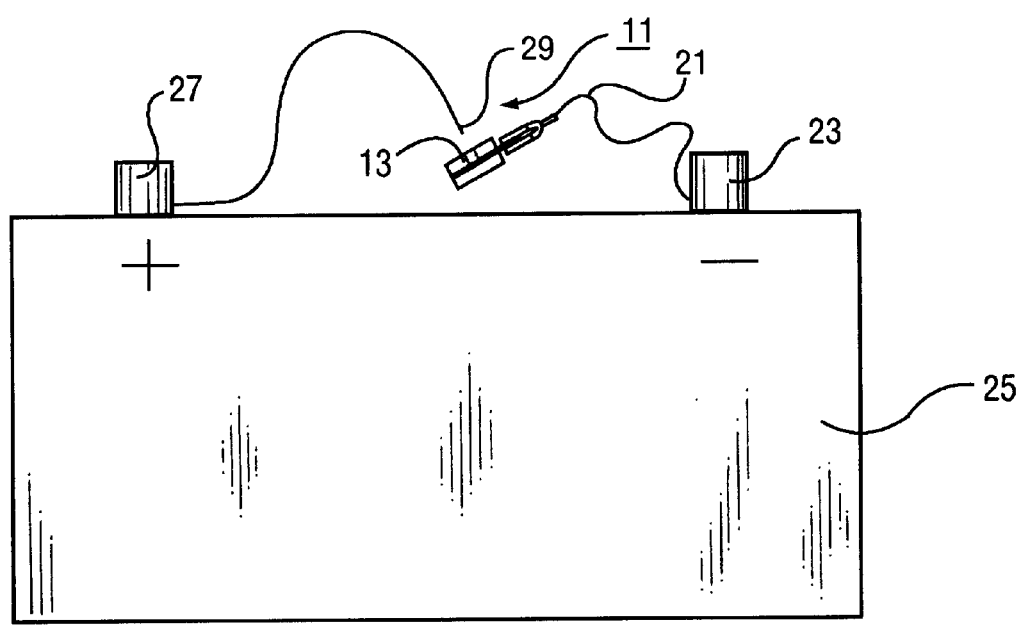
FIG. 1 is a simplified perspective view of an apparatus used for practicing the method of the invention.
Figures 2, 3:
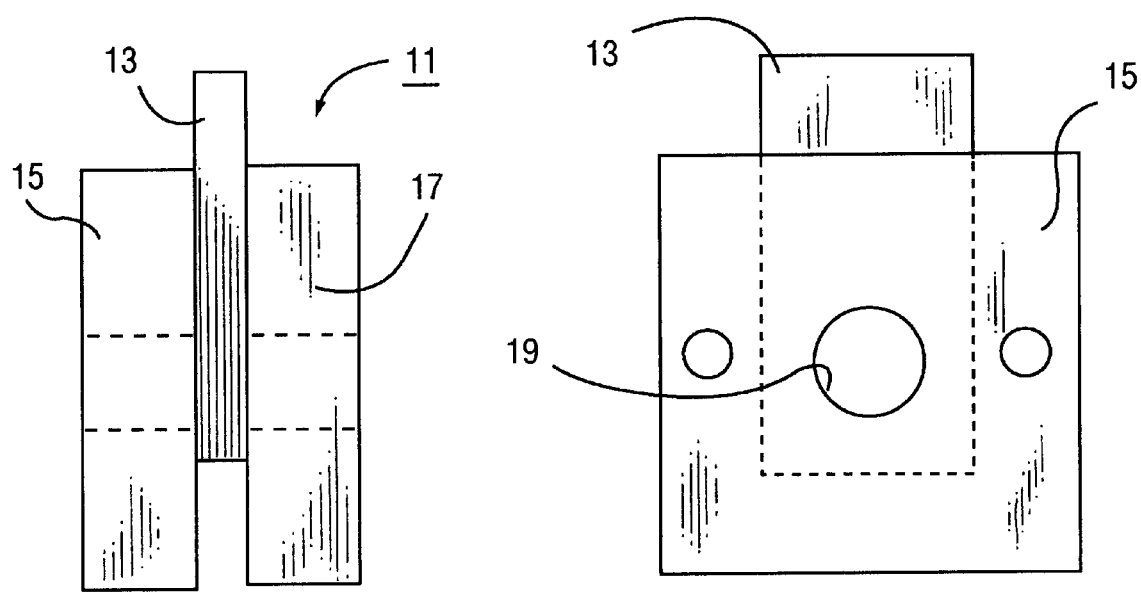
FIG. 2 is a top view of the fixture used to mount the silicon substrate used in the method of the invention.
FIG. 3 is a side view of the fixture of FIG. 2.

Turning to FIG. 1, there is shown an apparatus for practicing the method of the invention. The apparatus includes a jig or fixture 11 for mounting a silicon wafer 13. As shown in FIGS. 2 and 3, the silicon wafer 13 can be sandwiched between upper and lower ceramic insulating layers 15, 17 each of which is provided with one or more apertures 19. The sandwiched wafer is mounted by means of a clamp (21 in FIG. 1) which is electrically connected to the counter electrode 23 of a commercially available Tesla coil 25. The counter electrode 27 of the Tesla coil is connected to a nickel wire 29, the outer extent of which is positioned a short distance from the upper surface of the silicon wafer 13. While the prototype apparatus illustrated in FIG. 1 includes a single point electrode terminating in the point 29, it will be understood that other arrangements are possible. For example, a metal grid might be provided including a large number of projecting points evenly distributed across the grid. Alternatively, a wire bundle might be utilized with the wire tips pointing at the surface of the silicon wafer with the wire bundle being distributed such that the projection of the wire tips on the surface of the silicon wafer constitutes an evenly distributed dot pattern. The substrate might also be moved relative to the tip of the electrode or electrodes or the electrodes might move relative to a stationary substrate. The distance between the tip or tips of the electrode member 29 and the exposed top surface of the wafer 13 is on the order of ⅛ to ½ inch, preferably on the order of about ⅜ inch.

The Tesla transformer 25 may be a commercially available high-frequency transformer, such as the vacuum testers used for leakage tests in vacuum glass applications. Tesla coils will be familiar to those skilled in the art and are air-core resonant transformers. Working at high frequencies, they can generate voltages with spectacular lightning-like discharges. The energy pulses produced by the Tesla coil come from the primary circuit, illustrated in schematic formation in FIG. 4. The circuit includes a high voltage transformer 31, a primary capacitor 33, a spark gap 35 and a primary coil 37. The transformer 31, powered by the AC source 39 charges the capacitor 33 until there is a high enough voltage across the spark gap 35 to jump the air gap. When this spark occurs, the energy stored in the capacitor is "dumped" into the primary inductor 37. The primary inductor 37 then builds up a magnetic field as the capacitor's energy flows through the inductor. The magnetic field will eventually collapse and will, in turn, dump its remaining energy back into the capacitor 33. This alternating activity continues until there is insufficient voltage left to jump the spark gap. The oscillating frequency is chiefly determined by the value of the primary capacitor 33 and the primary inductor 37. Together, they form a parallel-resonant circuit. In a typical Telsa coil design, the frequency is adjusted by altering the primary coil's inductance.

If the described energy bursts are of the same frequency as the secondary, the energy transferred by the primary coil's magnetic field will start to build up in the secondary coil. Much like a laser, this energy grows and amplifies itself until a large voltage is built up at the top of the coil, which is dissipates into the air in the form of an electrical spark or sparks.

In the method of the invention, the distance between the electrode point 29 in FIG. 21 and the wafer substrate 13 effectively forms the "spark gap", referred to as 35 in FIG. 3. The spark gap of the Tesla coil thus subjects the isolating substrate and calcium phosphate coating to a high voltage spark, whereby a fixed calcium phosphate film having a desired morphology and thickness is formed within the selected region of the substrate. By "fixed" is meant that the calcium phosphate film is permanently or semi-permanently applied to the silicon substrate such that it will adhere and not, for example, be removed in a water wash.

The Tesla voltage applied is generally between about 10 and 100 KV preferably about 50 KV at a frequency ranging from about 400 to 500 kHz, with the power density being between about 0.1 and 100 W/cm$^2$. The duration of exposure ranged from about 30 minutes to 240 minutes with the preferred exposure being about 30–60 minutes at full power. The affected area was a circular region from about 1/16 to 5/32 inches in diameter. The edge definition of the pattern generated during the deposition step generally improves as the distance between the electrode and wafer surface is decreased. The deposition rate may be controlled, as desired, by varying the following parameters, among others: (1) the distance between the electrode or counterelectrode and top surface of the wafer substrate; (2) the power density and duration of the spark; and (3) the nature and pressure of the gas atmosphere surrounding the wafer substrate. The layers of film which are formed may have a thickness on the order of micrometers.

The invention, as illustrated in FIG. 1, may apply a film at normal pressure in air by means of a commercially available Tesla transformer without complicated alignment means. The device necessary for the implementation is thus very simple in design and economical to manufacture. It will be understood, however, that the device may also include an evacuatable reaction chamber in which the substrate is deposited and at which a gas inlet may be provided for adding defined quantities of inert gas. The rate of film deposition may then be controlled as a function of the gas pressure and the gas used. The method may also be practiced in a partial vacuum.

In another aspect of the invention, the calcium phosphate film which is deposited upon the silicon substrate is impregnated with an active agent which is intended to be released over a predetermined time interval. Preferably, the impregnating agent is a medicinally active agent. In one embodiment of the invention, the impregnating agent is cis-Platin, a drug used in treating certain forms of cancer and sold commercially as "PLATINOL", a trademark of Bristol Meyers Squibb. The step of impregnating the calcium phosphate film can comprise any convenient means, for example, immersing the silicon substrate with its applied film in a solution of the active drug ingredient; spin coating the wafer with the solution; applying the solution drop wise to the film on the wafer; and prior grinding of the drug in the powdered form with the calcium phosphate prior to applying the calcium phosphate film to the silicon substrate. The film formed on the silicon substrate has a characteristic porosity which is selected based upon the nature of the impregnating agent and the time interval over which it is to be released.

Figure 4:
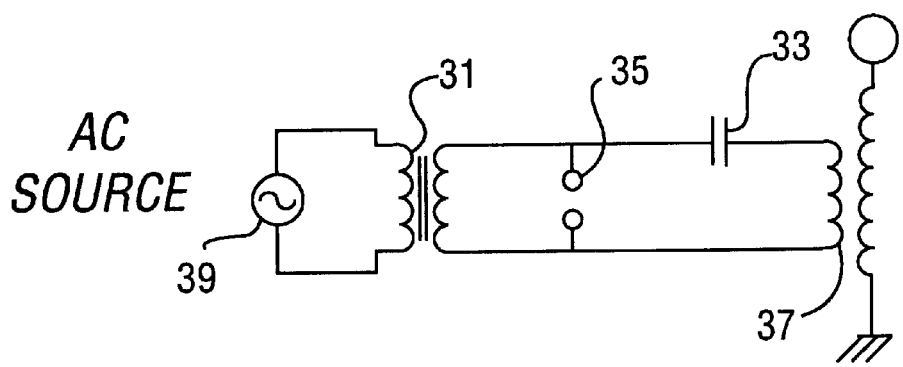
FIG. 4 is a simplified, schematic view of a Tesla coil of the type used in the method of the invention.
Figure 5:
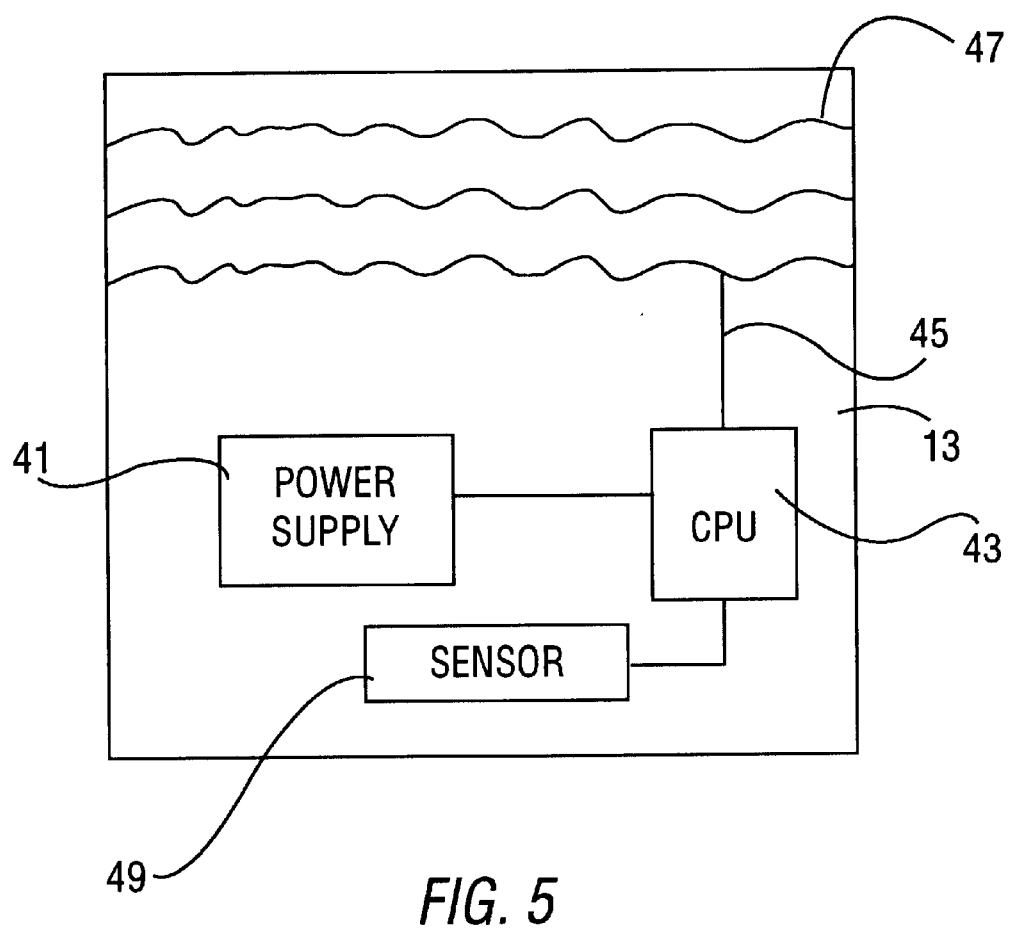
FIG. 5 is a simplified, schematic view, greatly enlarged, showing the components of the electrical actuating means used to dispense an active agent from the porous film formed on the substrate of the invention.

As shown in FIG. 5, the silicon substrate can also be provided with electrical actuating means for effecting the release of the active agent from the porous coating at preselected intervals. The electrical actuating means could be as simple as a simple timing circuit which could actuate the porous layer after a predetermined time interval. The preferred electrical actuating means illustrated in FIG. 4 includes as components thereof at least a power supply 41, a CPU 43 and an electrical connection 45 to the calcium phosphate film 47, all of which components are integrally formed within or mounted upon the semiconducting substrate 13. In its most preferred form, the electrical 49 actuating means includes a sensor 49 for detecting selected environmental conditions, the sensor 49 being electrically connected to the CPU, whereby the sensor causes the CPU to trigger a release of the active agent upon detection of a preselected environmental condition.

For example, the silicon wafer 13 illustrated in FIG. 4 might be surgically implanted or otherwise introduced within the body of a human being, or other living creature. The sensor 49 could constitute a simple timing circuit or could actually detect conditions such as the pH of the internal environment, the presence of a hormone or change in hormonal balance or other triggering signals which would cause the CPU to send an electrical signal to the calcium phosphate film 47. The CPU would monitor the level of the hormone and when a predetermined level was reached, the CPU would send a signal to effectuate the release the medicinally useful material. This signal could constitute, for example, the activation of resistive heating elements which would cause the active agent to be discharged from the pores of the film.

An example of an actual laboratory procedure used in evaluating the method of the invention will now be presented.

Figure 6:
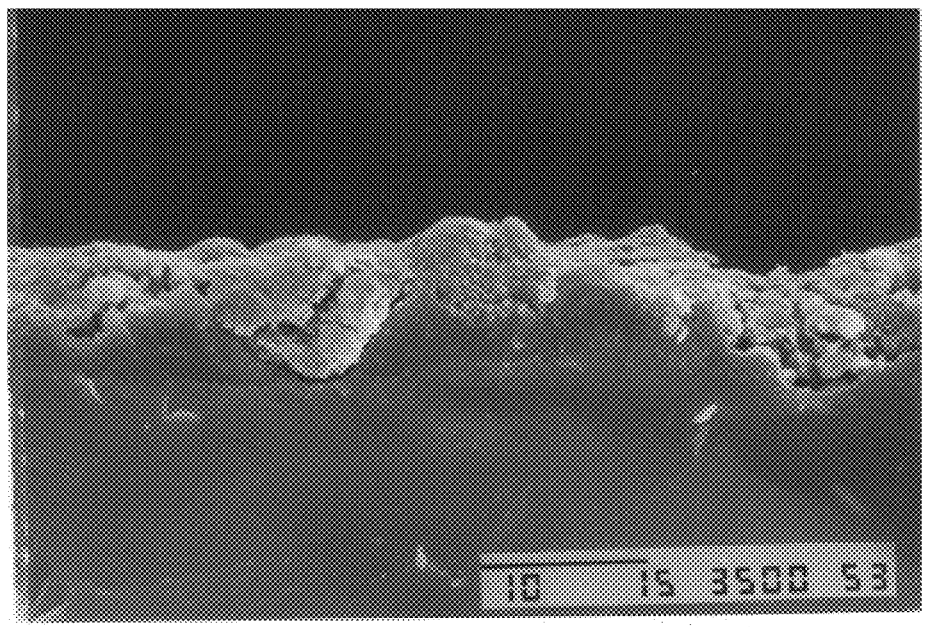
FIG. 6 is an SEM image of an approximate 5 micron calcium phosphate film formed on silicon using the method of the invention with an approximate ⅛ inch spark gap.
Figure 7:
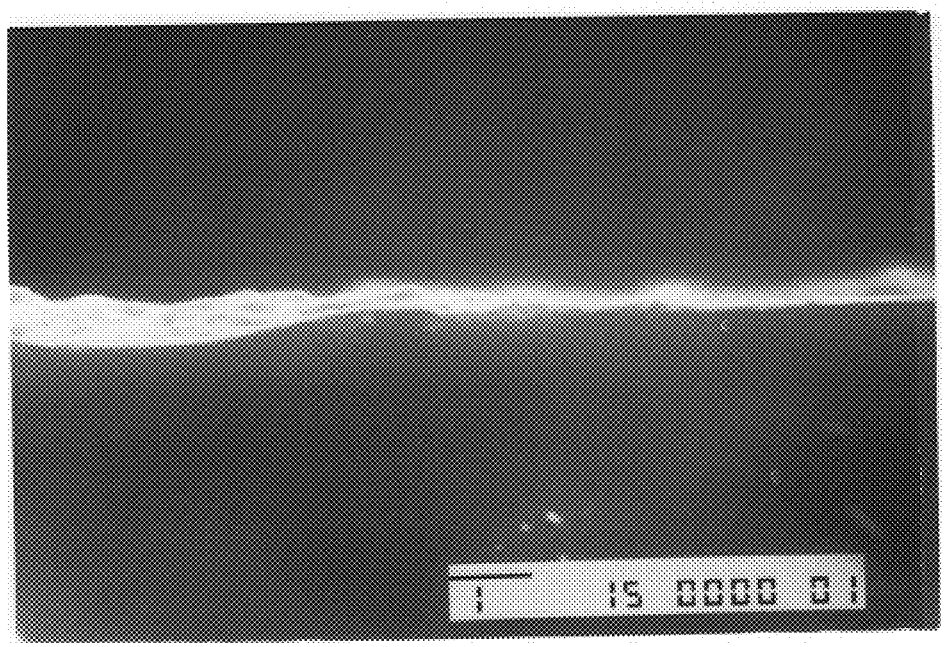
FIG. 7 is another SEM image of an approximate 100 nm calcium phosphate film using the method of the invention with an approximate ⅜ inch gap.
Figure 8:
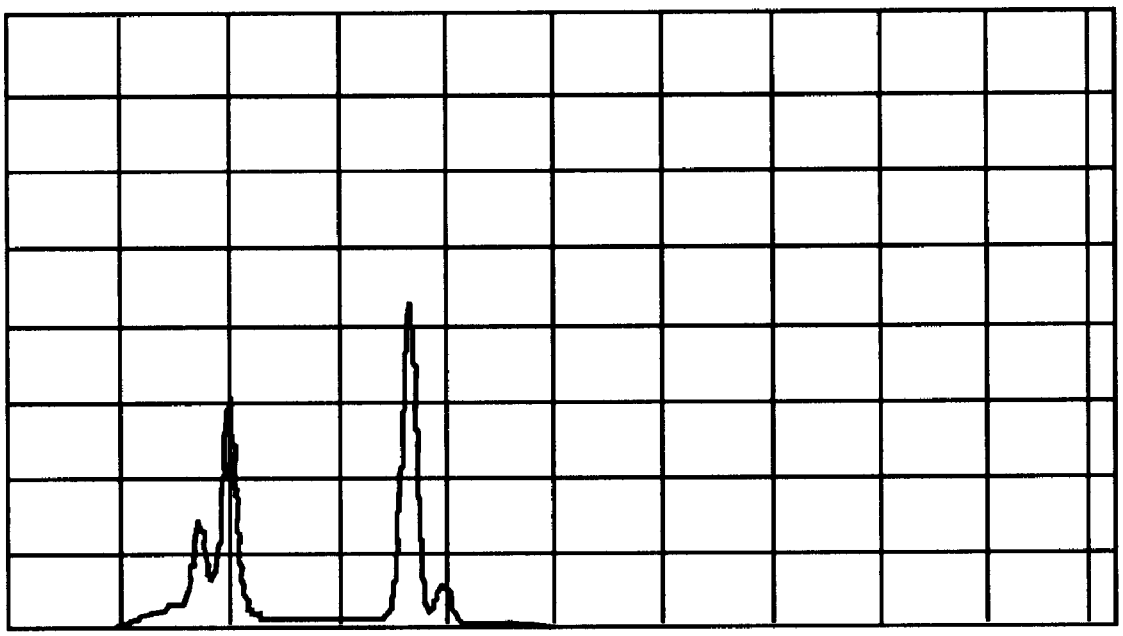
FIG. 8 is an X-ray energy dispersive spectrum of a calcium phosphate film formed on a silicon substrate using the method of the invention.

The technique was used for applying a calcium phosphate (Ca—P) film to a silicon (Si) substrate. The particular calcium phosphate utilized was hydroxyapatite, $Ca_{10}(PO_4)_6(OH)_2$. The first step of the procedure was to expose the Si substrate to the Ca—P to form a Ca—P coating on the Si substrate. Ca—P is used not only because it is porous but, as has been mentioned, because it is the inorganic component of bone and therefore produces little to no reaction in the human body. The Si substrate is used because it is compatible with existing integrated circuit processing methods. The Ca—P coating was applied by covering the Si substrate in a Ca—P/acetone slurry through capillary action. The slurry was prepared in a watch glass with 130 mg of Ca—P powder and 1 mL of acetone. The Si substrate was then placed face down on the slurry to draw the Ca—P onto the Si substrate through capillary action. A pipette was used to get more Ca—P onto the Si substrate. The sample was then allowed to air dry. Once dry, the Si substrate coated with the Ca—P was attached, with an alligator clip, to one electrode of a Tesla coil and a 6-inch piece of nickel wire was attached to the counterelectrode. A ceramic insulator was used to help focus the spark and obtain more consistent samples. Then the Si substrate coated with the Ca—P was subjected to a spark for a predetermined time interval, voltage, and distance from the Si substrate coated with the Ca—P to the counterelectrode. The morphology and thickness of the resulting Ca—P film on the Si substrate was determined by the duration of the spark, intensity of the spark and distance between the Si substrate coated with the Ca—P and the counterelectrode. FIGS. 6 and 7 are images taken by scanning electron microscopy of calcium phosphate films formed on silicon wafers using the method of the invention. FIG. 8 is an X-ray energy dispersive spectrum of a calcium phosphate film formed on a silicon substrate showing the presence of elemental calcium and phosphorous as well as silicon.

In order to reduce organic contaminants in the resulting Ca—P film, a dry method may also be used. In the dry method, the Si substrate is placed into a ceramic insulator and Ca—P powder is placed into the hole of the ceramic insulator. The powder is then compressed using an appropriately sized gauge pin. Once the powder is compressed, the sample is then subjected to a spark for a predetermined time interval, power level, and distance from the Si substrate coated to the counterelectrode. While the organic or other possible contaminants in the resulting Ca—P film are reduced, the dry method generally produces a lower Ca—P concentration on the Si substrate than the slurry application method.

After the Ca—P film has been anchored to the Si substrate by the spark, the resultant porous layer can be impregnated with any material capable of being received and stored in the porous layer, such as a medicinally useful active agent. The medicinally useful active agent impregnated in the porous Ca—P film can then be released by means of the previously described electrical actuating means.

To test the diffusion rates from the Ca—P film anchored to the Si substrate, small amounts of the cis-Platin cancer treatment drug (Cis-Pt) in solution form were applied to the Ca—P film. A fresh 10 mM solution of cis-Pt was prepared in de-ionized water for every diffusion experiment to prevent hydrolysis of the cis-Pt while still in solution. The samples were allowed to dry overnight before diffusion of the cis-Pt out of the Ca—P matrix. Diffusion experiments were done using a UV spectrophotometer and the spectra was recorded for three hours. It was found that most of the cis-Pt comes out of the matrix between the first and second hour of diffusion. It is necessary to utilize an aqueous based slurry in such situations to avoid organic contamination.

An invention has been provided with several advantages. The method and device of the invention provide a simple and economical means for applying a calcium phosphate film to a silicon substrate. The films are biocompatible and can be used to dispense medicinally active agents over a predetermined time interval. The method can be practiced using wet application techniques or using dry techniques where contamination of the underlying substrate is of concern. The device used to practice the invention may be used at normal pressure in an air atmosphere or may be enclosed in an evacuatable chamber which can be filled with an inert gas. By utilizing the electrical actuating means of the invention, more precisely time delivery of a drug, such as cis-Platin, can be achieved.

What is claimed is:

1. A method for the selective, self-aligned deposition of a calcium phosphate film to a selected region of an isolating substrate, the method comprising:

exposing the isolating substrate with calcium phosphate to form a coating;

subjecting the isolating substrate and calcium phosphate coating to a high voltage spark, such that a fixed calcium phosphate film having a desired morphology and thickness is formed within a selected region of the substrate.

2. The method of claim 1, wherein the isolating substrate is a semiconducting substrate.

3. The method of claim 2, wherein the semiconducting substrate is silicon.

4. The method of claim 1, wherein the calcium phosphate is provided in the form of a solvent slurry that is applied to the isolating substrate.

5. The method of claim 1, wherein the calcium phosphate is provided in the form of a dry, pressed powder that is applied to the isolating substrate.

6. A method for the selective, self-aligned deposition of a calcium phosphate film to a selected region of an isolating substrate, the method comprising:

exposing the isolating substrate with calcium phosphate to form a coating;

positioning an electrode a predetermined distance from the coating on the substrate;

generating a spark between the electrode and the coated substrate by capacitively coupling a RF power source to a selected one of the electrode and the coated substrate such that a fixed calcium phosphate film having a desired morphology and thickness is formed within the selected region of the substrate.

7. The method of claim 6, wherein the isolating substrate is a semiconducting substrate.

8. The method of claim 7, wherein the semiconducting substrate is silicon.

9. The method of claim 8, wherein the calcium phosphate is provided in the form of a solvent slurry that is applied to the isolating substrate.

10. The method of claim 9, wherein the calcium phosphate is provided in the form of a dry, pressed powder that is applied to the isolating substrate.

11. The method of claim 8, wherein the RF power source is supplied by attaching the selected one of the coated silicon substrate and the electrode to an electrically biased side of a Tesla coil.

12. The method of claim 11, wherein the step of generating a current comprises coupling a power source having a voltage of 10–100 kV, a frequency of 400–500 kHZ, and a power density of 0.1–100 W/cm2 to the selected electrode or substrate, and wherein a spacing between the electrode and the coated substrate ranges from about $\frac{1}{8}$ to $\frac{1}{2}$ inches.

13. The method of claim 8, wherein the step of generating a current is implemented in an atmosphere comprising air.

14. The method of claim 8, wherein the step of generating a current is implemented in an atmosphere comprising an inert gas.

15. A method for the selective, self-aligned deposition of a calcium phosphate film to a selected region of a silicon substrate, the method comprising:

exposing the silicon substrate with calcium phosphate to form a coating;

positioning an electrode a predetermined distance from the coating on the substrate;

generating a spark between the electrode and the coated substrate by capacitively coupling a RF power source to a selected one of the electrode and the coated substrate such that a fixed calcium phosphate film having a desired morphology and thickness is formed within the selected region of the substrate; and impregnating the calcium phosphate film with an active agent intended to be released over a predetermined time interval.

16. The method of claim 15 where the impregnating agent is medicinally active.

17. The method of claim 16, wherein the impregnating agent is cis-Platin.

18. The method of claim 16, wherein the film formed on the select region of the substrate has a characteristic porosity which is selected based upon the nature of the impregnating agent and the time interval over which it is to be released.

* * * * *